(12) United States Patent
Yin et al.

(10) Patent No.: US 12,343,466 B2
(45) Date of Patent: Jul. 1, 2025

(54) MULTIFUNCTIONAL CENTRAL SUCTION SYSTEM CAPABLE OF REMOTE MONITORING

(71) Applicant: TONGYE TECHNOLOGIES DEVELOPMENT CO., LTD, Tianjin (CN)

(72) Inventors: Hua Yin, Tianjin (CN); Jin Ma, Tianjin (CN); Ying Zhang, Tianjin (CN)

(73) Assignee: TONGYE TECHNOLOGIES DEVELOPMENT CO., LTD., Tianjin (CN)

( * ) Notice: Subject to any disclaimer, the term of this patent is extended or adjusted under 35 U.S.C. 154(b) by 332 days.

(21) Appl. No.: 17/417,926

(22) PCT Filed: May 18, 2020

(86) PCT No.: PCT/CN2020/090813
§ 371 (c)(1),
(2) Date: Jun. 24, 2021

(87) PCT Pub. No.: WO2020/238675
PCT Pub. Date: Dec. 3, 2020

(65) Prior Publication Data
US 2022/0088284 A1  Mar. 24, 2022

(30) Foreign Application Priority Data

May 30, 2019  (CN) .......................... 201910460436.1

(51) Int. Cl.
*A61M 1/00*  (2006.01)
(52) U.S. Cl.
CPC .............. *A61M 1/782* (2021.05); *A61M 1/73* (2021.05); *A61M 1/74* (2021.05);
(Continued)

(58) Field of Classification Search
CPC .......... A61M 1/73; A61M 1/74; A61M 1/782; A61M 2205/3331; A61M 2205/3393; A61M 2205/3553; A61M 2205/3584
See application file for complete search history.

(56) References Cited

U.S. PATENT DOCUMENTS

| 7,763,000 B2 * | 7/2010 | Risk, Jr. .................. | A61M 1/98 604/35 |
| 2007/0135779 A1 * | 6/2007 | Lalomia .................. | A61M 1/60 604/319 |

(Continued)

FOREIGN PATENT DOCUMENTS

| CN | 1867373 A | * | 11/2006 | ........ A61M 16/0677 |
| CN | 101227937 A | * | 7/2008 | .......... A61M 1/0001 |

(Continued)

OTHER PUBLICATIONS

International Search Report issued Aug. 11, 2020, in International (PCT) Application No. PCT/CN2020/090813, with English translation.

*Primary Examiner* — Rebecca E Eisenberg
*Assistant Examiner* — Kate Elizabeth Strachan
(74) *Attorney, Agent, or Firm* — WENDEROTH, LIND & PONACK, L.L.P.

(57) ABSTRACT

A multifunctional central suction system capable of remote monitoring includes a flow measurement device and a controller, wherein a negative pressure port of the flow measurement device is connected to a negative pressure air nozzle of the controller via a gas pipe; the flow measurement device includes a measurement mechanism and a liquid bottle; the negative pressure port is arranged on the liquid bottle; a first BLUETOOTH® communication module is provided on the measurement mechanism; a communication module is provided in the controller; the communication module includes a second BLUETOOTH® communication (Continued)

module and a Wi-Fi® communication module; and the first BLUETOOTH® communication module on the measurement mechanism is in communication connection with the second BLUETOOTH® communication module in the controller.

13 Claims, 18 Drawing Sheets

(52) U.S. Cl.
CPC .............. *A61M 2205/3331* (2013.01); *A61M 2205/3393* (2013.01); *A61M 2205/3553* (2013.01); *A61M 2205/3584* (2013.01)

(56) References Cited

U.S. PATENT DOCUMENTS

| | | | |
|---|---|---|---|
| 2010/0022990 A1 | 1/2010 | Karpowicz et al. | |
| 2015/0290364 A1* | 10/2015 | Wall | A61M 1/96 604/23 |
| 2017/0275044 A1* | 9/2017 | Arregui Letamendi | B65D 1/0223 |
| 2019/0201046 A1* | 7/2019 | Shelton, IV | A61B 17/1114 |
| 2019/0307272 A1* | 10/2019 | Newell | A61J 9/001 |
| 2019/0381220 A1* | 12/2019 | Locke | A61M 1/60 |
| 2019/0388279 A1* | 12/2019 | Hartwell | A61F 13/0216 |

FOREIGN PATENT DOCUMENTS

| | | | |
|---|---|---|---|
| CN | 201379828 Y | * | 1/2010 |
| CN | 101810534 A | * | 8/2010 |
| CN | 201871002 | | 6/2011 |
| CN | 201959393 | | 9/2011 |
| CN | 201959393 U | * | 9/2011 |
| CN | 103528636 | | 1/2014 |
| CN | 106110417 B | * | 2/2018 |
| CN | 110251741 | | 9/2019 |
| WO | WO-2013123022 A1 | * | 8/2013 ....... A61F 13/00068 |

* cited by examiner

MULTIFUNCTIONAL CENTRAL SUCTION SYSTEM CAPABLE OF REMOTE MONITORING

TECHNICAL FIELD

The present disclosure belongs to the field of medical apparatus, and relates to a central suction system, in particular to a multifunctional central suction system capable of remote monitoring.

BACKGROUND ART

A central suction apparatus, also referred to as a central negative pressure suction apparatus, is a medical apparatus frequently used in clinical medicine, which is generally configured for sucking blood, body fluid, secretions, soft tissue, etc. of a patient, and is used widely in clinical application in the world as a technique for assisting in treating wound to heal.

In the clinic, it is necessary to measure liquid drained out by the central suction apparatus in real time, suction amount (i.e. instantaneous fluid volume) of human tissue fluid during treatment may be monitored so as to ensure safety of a patient during treatment. Once the instantaneous fluid volume is beyond a normal value, it may be indicated that an abnormality occurs in the patient's condition, and if the abnormality cannot be detected and treated in time, it is highly likely to cause harm to the patient's life safety.

Currently, in clinical practice, real-time measurement technology for sucking liquid under negative pressure is not yet mature, and has undesirable safety, reliability and timeliness. Therefore, it is desirable to design a safe and reliable central suction system with high control accuracy, a capability of real-time measurement of drainage liquid, and a function of remote monitoring.

By searching for the published patent document, no published patent document identical to this patent application is found.

SUMMARY

An object of some embodiments is to overcome the defects of the prior art, and to provide a multifunctional central suction system, which has advantages of high safety and high pressure control accuracy, being capable of performing remote monitoring and measuring a flow of drainage liquid in real time, and being easy to be implemented.

The above technical problem is solved by adopting the following technical solutions:

It is provided a multifunctional central suction system capable of remote monitoring, which includes a flow measurement device and a controller. A negative pressure port of the flow measurement device is connected to a negative pressure air nozzle of the controller via a gas pipe. The flow measurement device includes a measurement mechanism and a liquid bottle. The negative pressure port is arranged on the liquid bottle, and the measurement mechanism is provided with a first BLUETOOTH® communication module. A communication module including a second BLUETOOTH® communication module and a Wi-Fi® communication module is provided in the controller. The first BLUETOOTH® communication module on the measurement mechanism is in communication connection with the second BLUETOOTH® communication module in the controller.

In some embodiments, the measurement mechanism on the flow measurement device may include a base, a weighing monitoring unit, a bracket and a battery. The weighing monitoring unit may be powered by the battery arranged in the base. A weighing sensor of the weighing monitoring unit may be provided on the base. The bracket is provided above the weighing sensor. Baffle plates may be evenly and circumferentially disposed at an interval on an upper end surface of a bracket body of the bracket. An area surrounded by the baffle plates forms a liquid bottle mounting area. The liquid bottle may be mounted into the liquid bottle mounting area.

In some embodiments, the base may be a groove-type base. A guard plate protruding upward may be provided at a first side in a groove of the groove-type base, a weighing sensor may be provided at a second side opposite to the first side in the groove, the weighing sensor may be perpendicular to the guard plate in a plane, and a height of the weighing sensor may be higher than a height of the guard plate, a height difference between the weighing sensor and the guard plate may be 1 mm.

In some embodiments, the bracket may include an upper supporting plate and a lower supporting plate provided in one piece. A bottom of the lower supporting plate may be provided with limiting protrusions assembled at two ends of the weighing sensor, a mounting groove may be arranged in a middle of the upper supporting plate, mounting through holes leading to the lower supporting plate may be arranged in the mounting groove and be located between two limiting protrusions. The bracket may be assembled with the weighing sensor in the base via screw passing through the mounting through holes. The baffle plates forming a ring adapted to an outer diameter of a bottom of the liquid bottle may be arranged circumferentially on the upper supporting plate.

In some embodiments, the measurement mechanism further includes a protection frame. The protection frame includes a shell integrally formed with the base, a protection frame body arranged on an inner wall of the shell, and a guard ring arranged on an inner periphery of the protection frame body via a mounting block.

In some embodiments, the weighing monitoring unit may mainly include the weighing sensor, a first CPU, a signal processor, a first display module, the first BLUETOOTH® communication module and a first alarm module. An output terminal of the weighing sensor may be connected to an input terminal of the signal processor. The output terminal of the signal processor may be connected to the first CPU. The first BLUETOOTH® communication module may be provided on the first CPU. An output terminal of the first CPU may be connected to the first display module and the first alarm module. The first display module may include a measurement liquid crystal display and a key mounted on the base.

In some embodiments, the base may be further provided with a charging port thereon.

In some embodiments, the liquid bottle may include a bottle body, a bottle cap, an overflow-proof protection mechanism and a full liquid protection mechanism. The overflow-proof protection mechanism may include an overflow-proof plug and a splash-proof baffle. The bottle cap may be arranged on the bottle body and provided with a liquid inlet and a negative pressure port. The overflow-proof plug may be arranged at the negative pressure port at a bottom of the bottle cap. The splash-proof baffle may be arranged between the overflow-proof plug and the liquid inlet. The full liquid protection mechanism may include a photoelectric sensor arranged on the protection frame and connected with the first CPU.

In some embodiments, the overflow-proof plug may include a conical floating head, a connecting rod, a float silicone head and a float basket. The float basket is mounted at a lower end of the negative pressure port, the connecting rod may be mounted to the float basket via the float silicone head for limiting, and the conical floating head is provided at a lower end of the connecting rod.

In some embodiments, the system further includes a liquid-pipe fixing clamp made of rubber and plastic material, the liquid-pipe fixing clamp includes a clamp head formed with a clamping slot and a mounting slide groove. The mounting slide groove is arranged on a back of the clamp head and clamped on the protection frame.

In some embodiments, the controller may include a housing, a pressure detection control module, a second CPU, a second display module and a key module. The housing may be provided sequentially with a negative pressure inlet and an oxygen inlet on a wall of a rear housing of the housing. A bottom of the housing may be provided sequentially with an oxygen outlet and a negative pressure outlet. The pressure detection control module may be provided in the housing. Various corresponding electromagnetic valves of the pressure detection control module may be connected to the negative pressure inlet, the oxygen inlet, the negative pressure outlet and the oxygen outlet via pipes, respectively. The pressure detection control module, the second display module and the key module may be respectively connected to the second CPU arranged inside the housing. A controller liquid crystal display of the second display module may be embedded into a front end surface of a front housing of the housing. The key module may be arranged below the second display module on the front housing.

In some embodiments, the pressure detection control module may include a negative pressure detection control unit. The negative pressure detection control unit may include a negative pressure regulating valve, a negative pressure inlet pressure sensor and a negative pressure outlet pressure sensor arranged on a valve plate. The negative pressure regulating valve may include a negative pressure intake valve, a negative pressure gulp valve, and a first vent valve. The negative pressure intake valve may be connected in series with the first vent valve and in parallel to the negative pressure gulp valve. A negative-pressure-inlet pressure sensor may be arranged on a pipe between the negative pressure inlet and the negative pressure regulating valve. A negative-pressure-outlet pressure sensor may be arranged on a pipe between the negative pressure regulating valve and the negative pressure outlet. The negative pressure regulating valve, the negative-pressure-inlet pressure sensor and the negative-pressure-outlet pressure sensor each may be connected to the second CPU.

In some embodiments, the pressure detection control module may further include an oxygen detection control unit. The oxygen detection control unit may include an oxygen regulating valve, an oxygen-inlet pressure sensor and an oxygen-outlet pressure sensor arranged on the valve plate. The oxygen regulating valve may include an oxygen intake valve and a second vent valve connected in series. An oxygen-inlet pressure sensor may be arranged on a pipe between the oxygen-inlet and the oxygen regulating valve. An oxygen-outlet pressure sensor may be arranged on a pipe between the oxygen regulating valve and the oxygen outlet. The oxygen regulating valve, the oxygen-inlet pressure sensor and the oxygen-outlet pressure sensor each may be connected to the second CPU.

In some embodiments, the negative pressure intake valve of the negative pressure regulating valve may include one negative pressure intake valve or more negative pressure intake valves connected in parallel.

In some embodiments, a sealing device may be provided at each valve port of the negative pressure regulating valve and the oxygen regulating valve.

In some embodiments, the system further includes an electronic overflow-proof module. The electronic overflow-proof module may include an overflow-proof device, an electrode circuit board, electrodes and an overflow-proof bottle. The overflow-proof device may be provided at the negative pressure outlet. Two electrodes may be mounted on the overflow-proof device and connected to the electrode circuit board. The electrode circuit board may be connected with the second CPU. The overflow-proof bottle covering an exterior of the electrodes may be arranged at the negative pressure outlet. A negative pressure air nozzle which is mounted by means of a sealing device may be provided on a bottle body of the overflow-proof bottle.

In some embodiments, the system may further include a second alarm module comprising an LED light covered by the overflow-proof bottle and a buzzer in the housing, and the LED light and the buzzer may be both connected to the second CPU.

The present disclosure has the following advantages and positive effects:

1. For the multifunctional central suction system capable of remote monitoring of the present disclosure, the controller can acquire data from the flow measurement device via the first BLUETOOTH® communication module and the second BLUETOOTH® communication module provided, and the data can be transmitted to a terminal such as Nurses Station via a Wi-Fi® module in the controller, thereby facilitating a nurse to monitor and ensuring safety of a patient during drainage.

2. For the multifunctional central suction system capable of remote monitoring of the present disclosure, installation stability of the liquid bottle is enhanced by mounting it on the bracket having the baffle plates, thereby facilitating metering instantaneous liquid volume and ensuring reliability of the measured data. Due to arrangement of the guard plate on the base and the height difference between the guard plate and the weighing sensor being 1 mm, which is an allowable deformation amount of the weighing sensor, a problem that the measurement accuracy is affected by the weighing sensor subject to a squeeze is avoided. With arrangement of the protection frame, installation stability of the liquid bottle is further ensured and the liquid bottle falling down caused by external interference can also be avoided. The measurement data can be displayed on the measurement LCD in real time to facilitate medical personnel to monitor, with arrangement of the display function. When an abnormal condition occurs, an alarm can be sent via the alarm.

3. For the multifunctional central suction system capable of remote monitoring of the present disclosure, the overflow-proof protection mechanism and the full liquid protection mechanism are arranged on a traditional liquid bottle having only a liquid collection function, to avoid operation performed under an overflow and full liquid state; such dual protection functions make the measurement device more convenient and reliable in use.

4. For the multifunctional central suction system capable of remote monitoring of the present disclosure, the liquid pipe fixing clamp is arranged to facilitate positioning liquid pipe and gas pipe and guarantee stability thereof, thereby avoiding the influence on the measurement accuracy caused due to a back-and-forth shake of the pipes.

5. For the multifunctional central suction system capable of remote monitoring of the present disclosure, besides controlling negative pressure air ingoing and outgoing, the controller can be configured to intermittently oxygenate a drainage wound based on clinical requirements, so as to promote better wound healing. An output negative pressure can be detected and controlled by cooperation of the electromagnetic valve group and each pressure sensor of the controller, i.e., the electromagnetic valve group is controlled through process of the second CPU. When an output value is lower than a predetermined value, the negative pressure gulp valve starts to supply air; when the output value is higher than the predetermined value, a first vent valve starts to discharge air; therefore, the output pressure value is always consistent with the predetermined pressure value, without being affected by fluctuations of the central negative pressure, the output negative pressure is maintained stable. During the intermission of negative pressure suction, central oxygen can be controlled by the present system according to a preset pressure and working time of the central oxygen; that is, the pressure at the oxygen output end is detected by the oxygen-outlet pressure sensor, and the electromagnetic valve group is controlled by the process of the second CPU, so that the output pressure at the output is always maintained at a predetermined pressure value, and a stable output of the oxygen is maintained without being affected by fluctuations of the central oxygen pressure. Through arrangement of the electronic overflow-proof module and the second alarm module, on the one hand, the safety of the present system in use can be enhanced, and on the other hand, the patient's condition, such as massive haemorrhage, can also be monitored and alarmed. When the liquid overflows into the overflow-proof bottle, the two metal electrodes become conductive. A resultant signal is processed by the second CPU, to drive the LED (Light Emitting Diode) light and the buzzer to realize sound and light alarm. Arrangement of the electrodes improves response speed to overflow monitoring, enables the output of the negative pressure to be switched off immediately to ensure safety in use. Furthermore, the LED light is provided to facilitate observation of the liquid amount in the overflow-proof bottle. The second alarm module may also have functions such as system leakage alarm, overpressure alarm, and pipeline blockage alarm.

6. For the multifunctional central suction system capable of remote monitoring of the present disclosure, the number of the negative pressure intake valves in parallel can be selectively increased, different numbers of the negative pressure intake valves may be turned on according to required negative pressure flow to meet various usage requirements.

7. The present disclosure has scientific reasonable design and advantages of high safety and high pressure control accuracy, being capable of realizing remote monitoring and measuring a flow rate of drainage liquid in real time, and being easy to be implemented, which is a multifunctional central suction system with high inventiveness.

Figure 1:
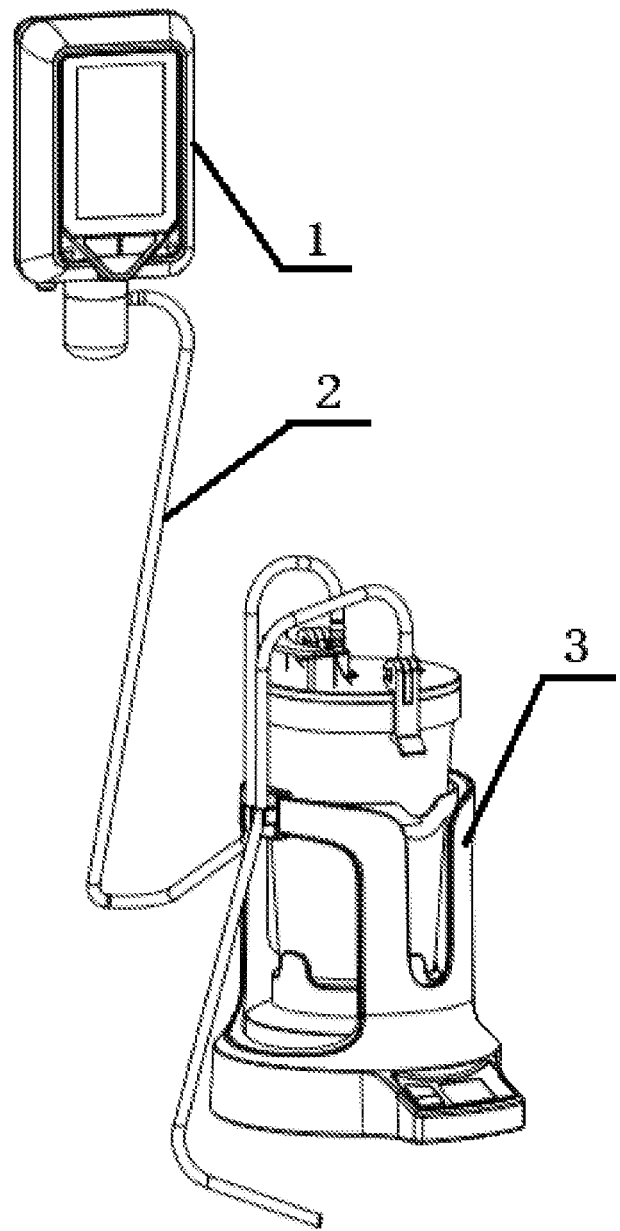
FIG. 1 is a structural schematic diagram of the present disclosure.
Figure 2:
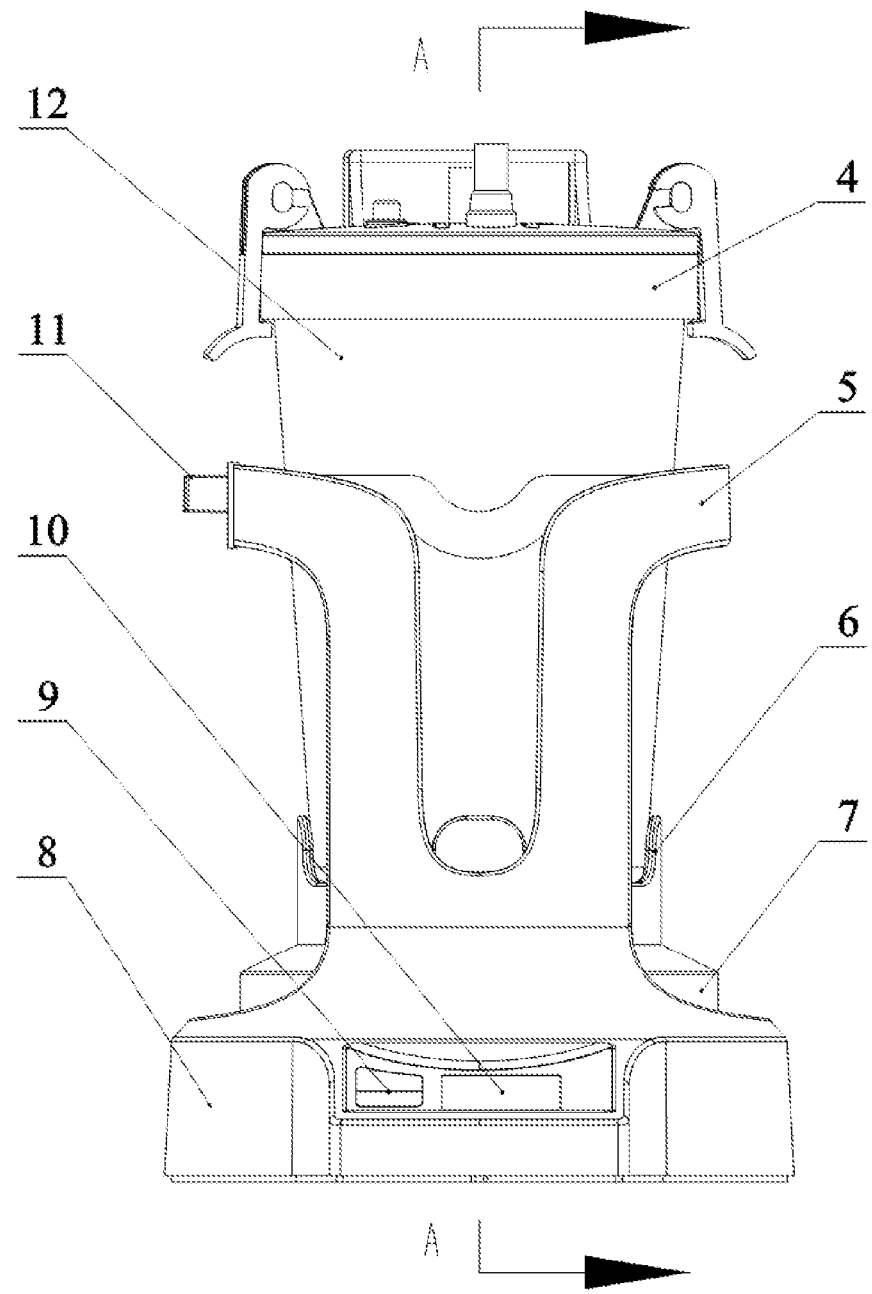
FIG. 2 is a structural schematic diagram of a flow measurement device according to the present disclosure.
Figure 3:
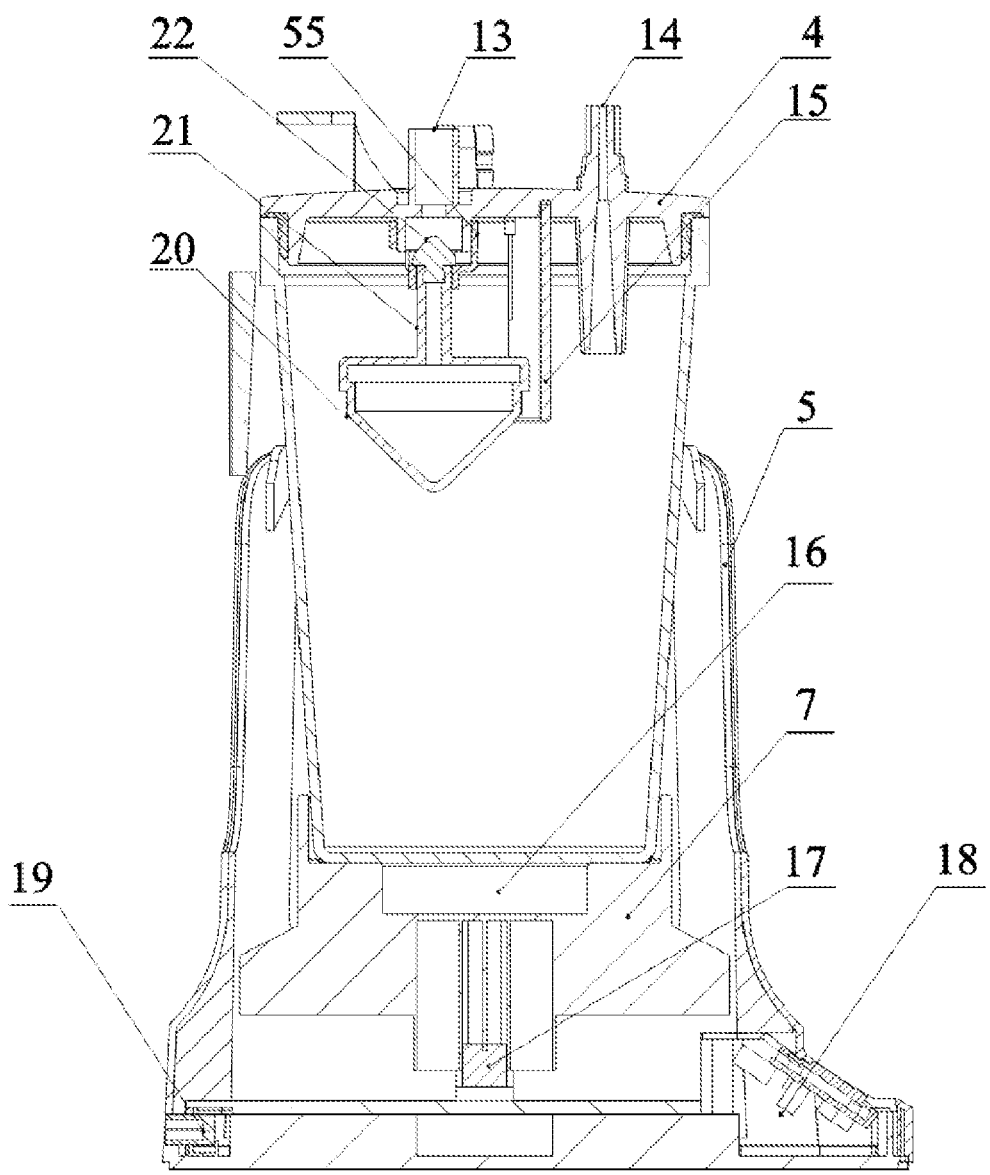
FIG. 3 is a cross-sectional view taken along a line A-A of FIG. 2.
Figure 4:
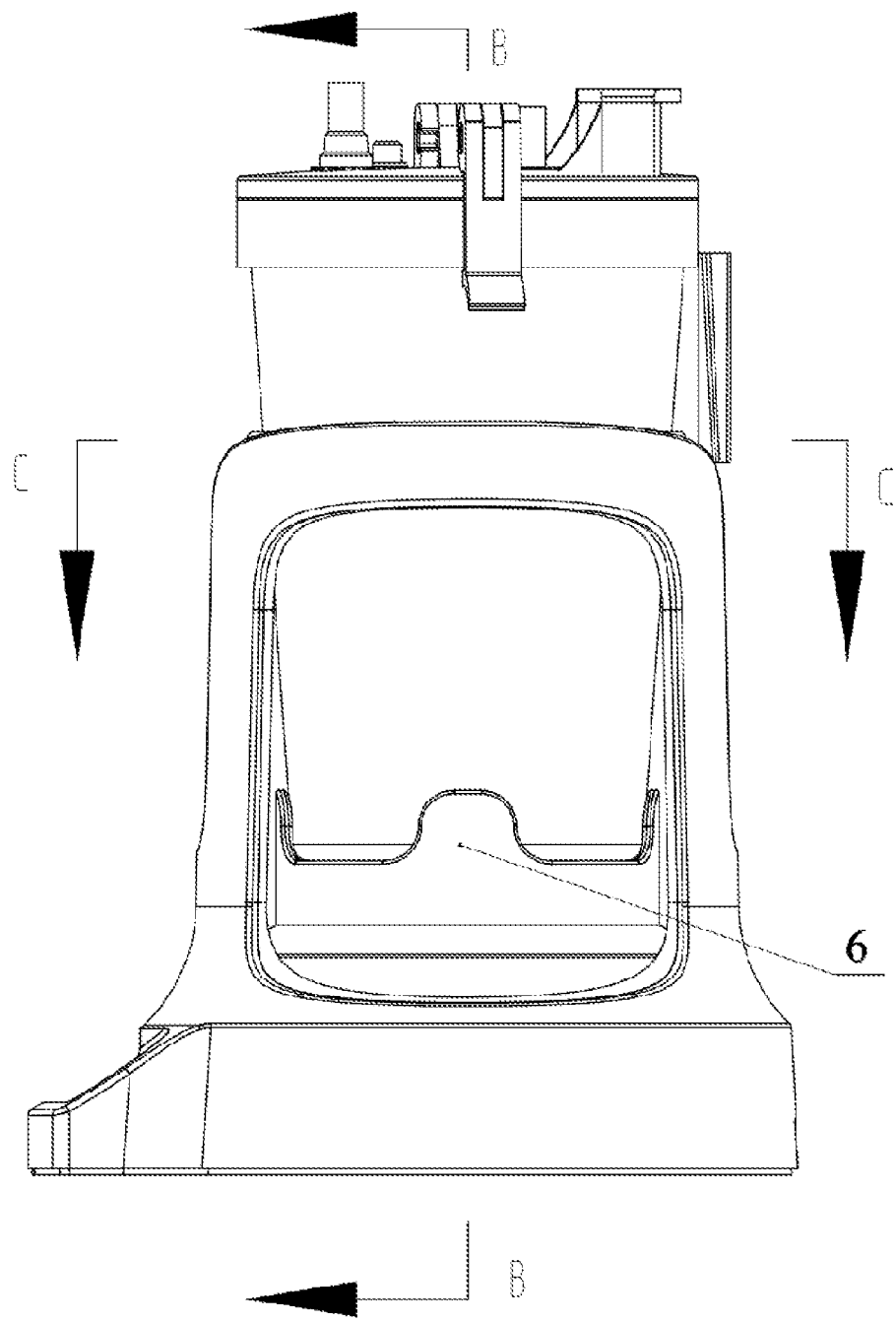
FIG. 4 is a right side view of FIG. 2.
Figure 5:
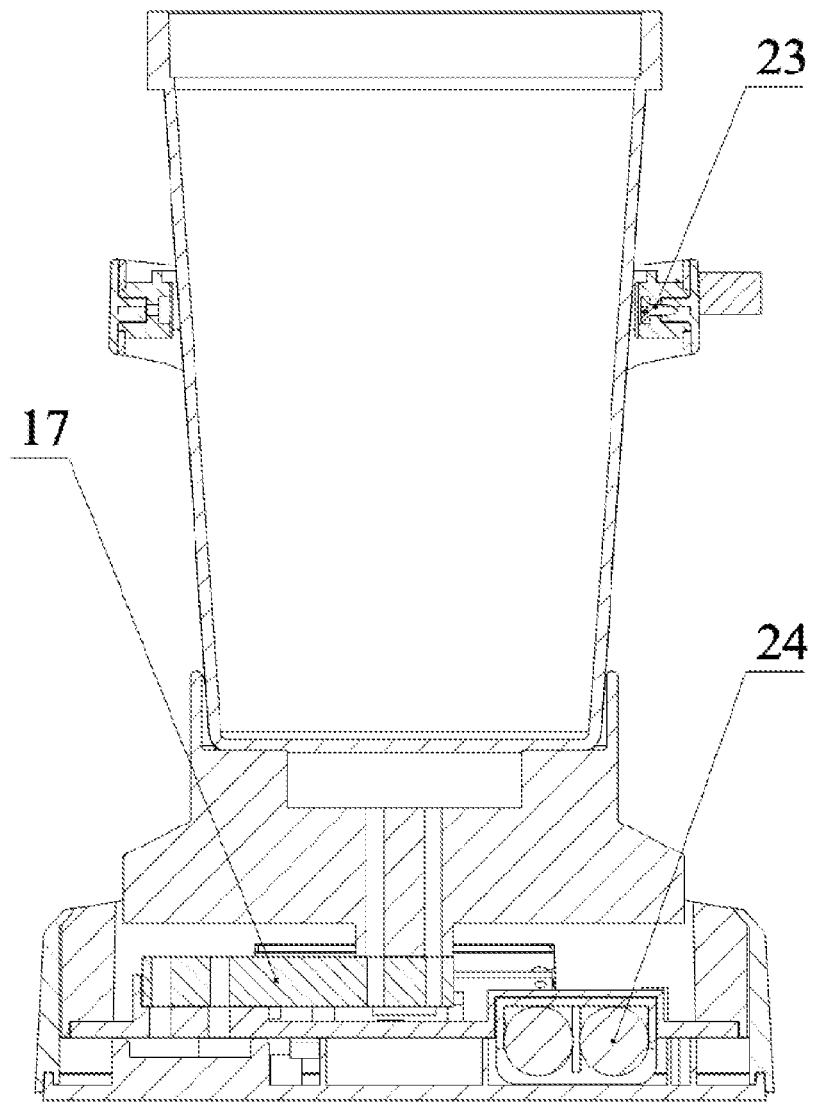
FIG. 5 is a cross-sectional view taken along a line B-B of FIG. 4, in which a bottle cap portion is omitted.
Figure 6:
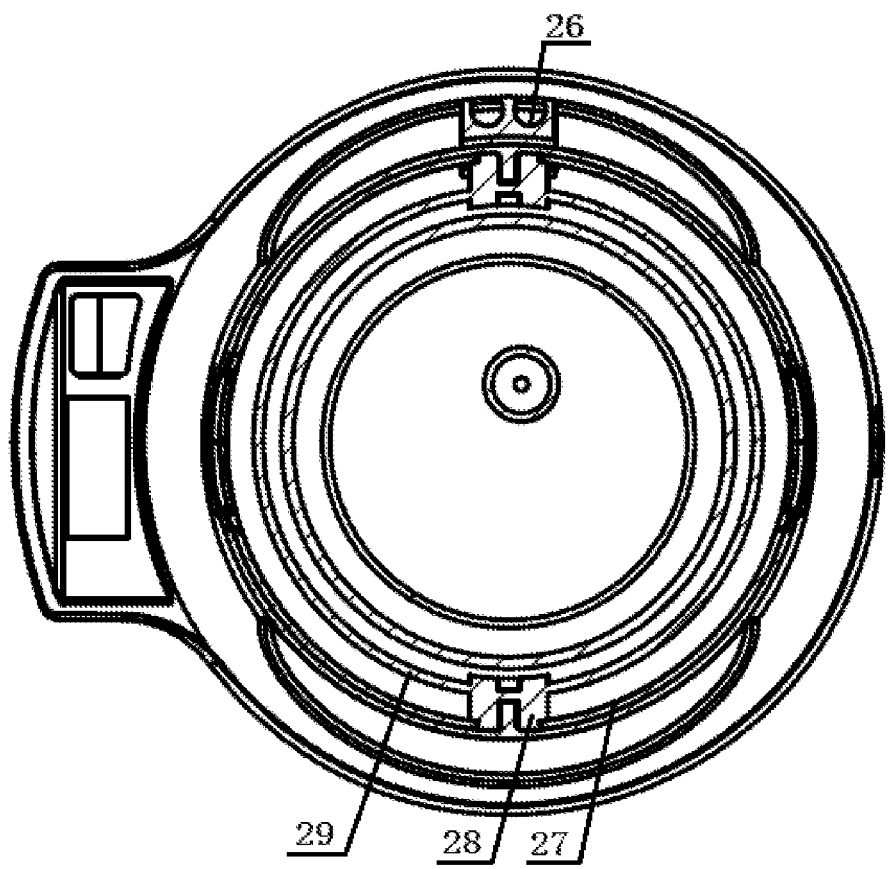
FIG. 6 is a cross-sectional view taken along a line C-C of FIG. 4.
Figure 7:
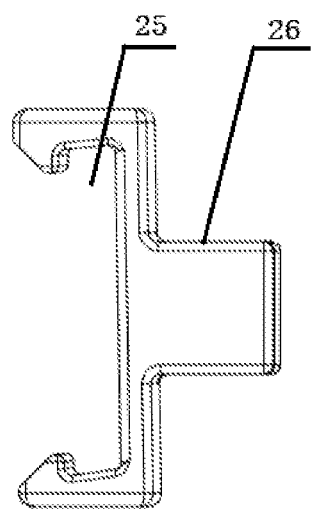
FIG. 7 is a structural schematic diagram of a liquid pipe fixing clamp according to the present disclosure.
Figure 8:
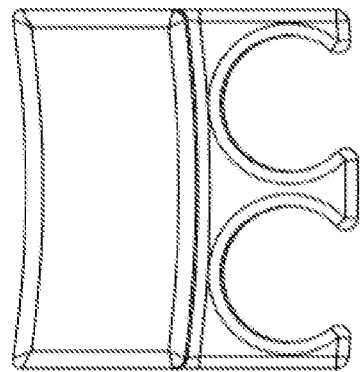
FIG. 8 is a top view of FIG. 7.
Figure 9:
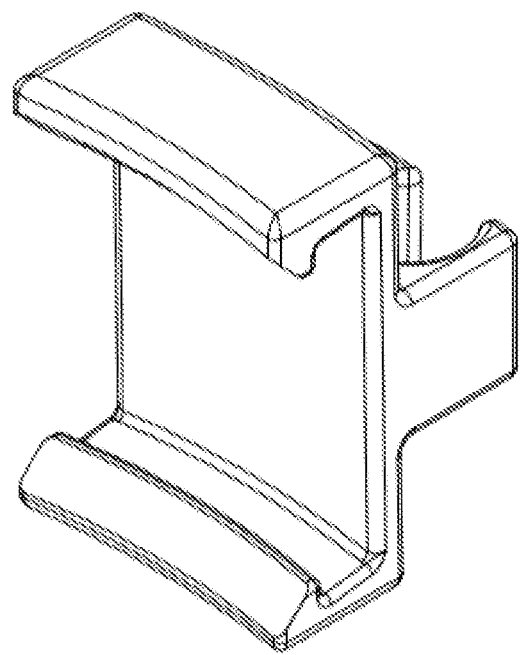
FIG. 9 is a perspective view of FIG. 7.
Figure 10:
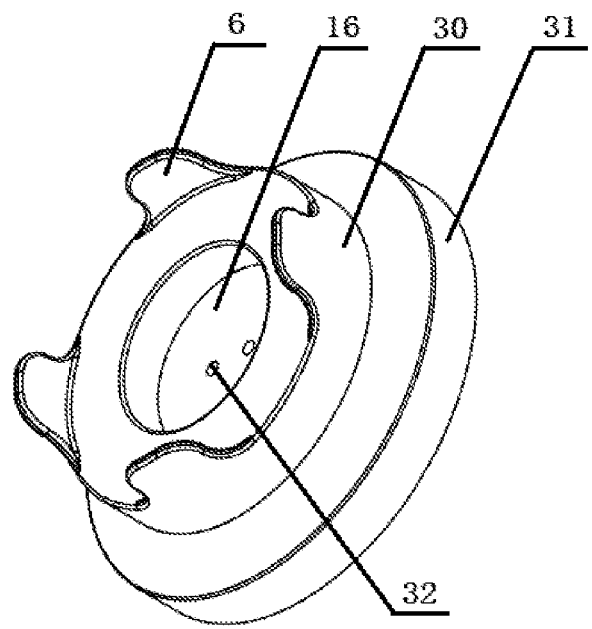
FIG. 10 is a perspective view of the bracket according to the present disclosure.
Figure 11:
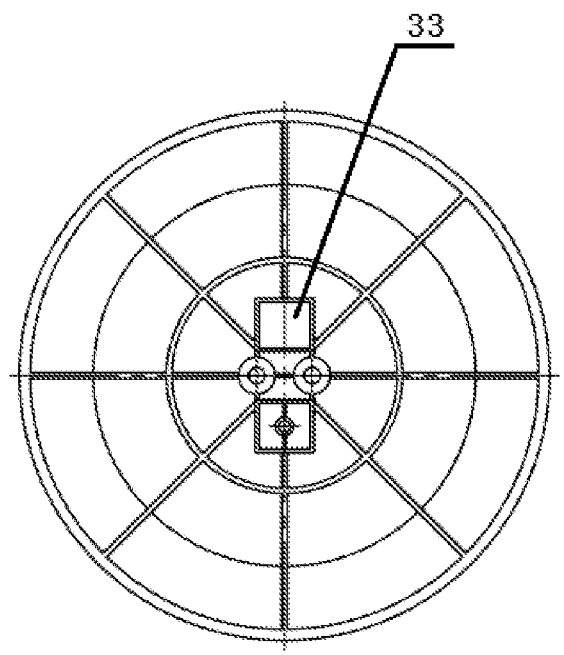
FIG. 11 is a bottom view of the bracket according to the present disclosure.
Figure 12:
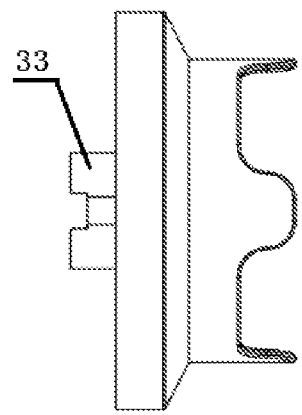
FIG. 12 is a right side view of FIG. 11.
Figure 13:
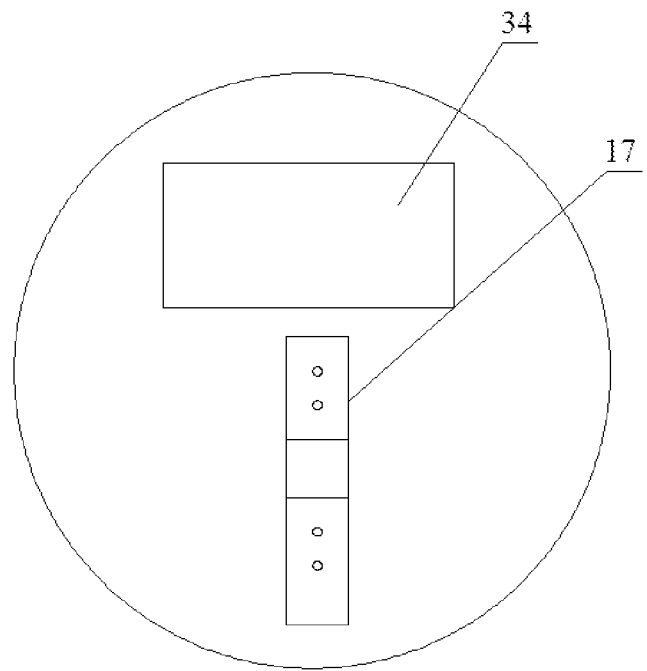
FIG. 13 is a structural schematic diagram of arrangement of a weighing sensor and a guard plate arranged in a groove in the flow measurement device according to the present disclosure.
Figure 14:
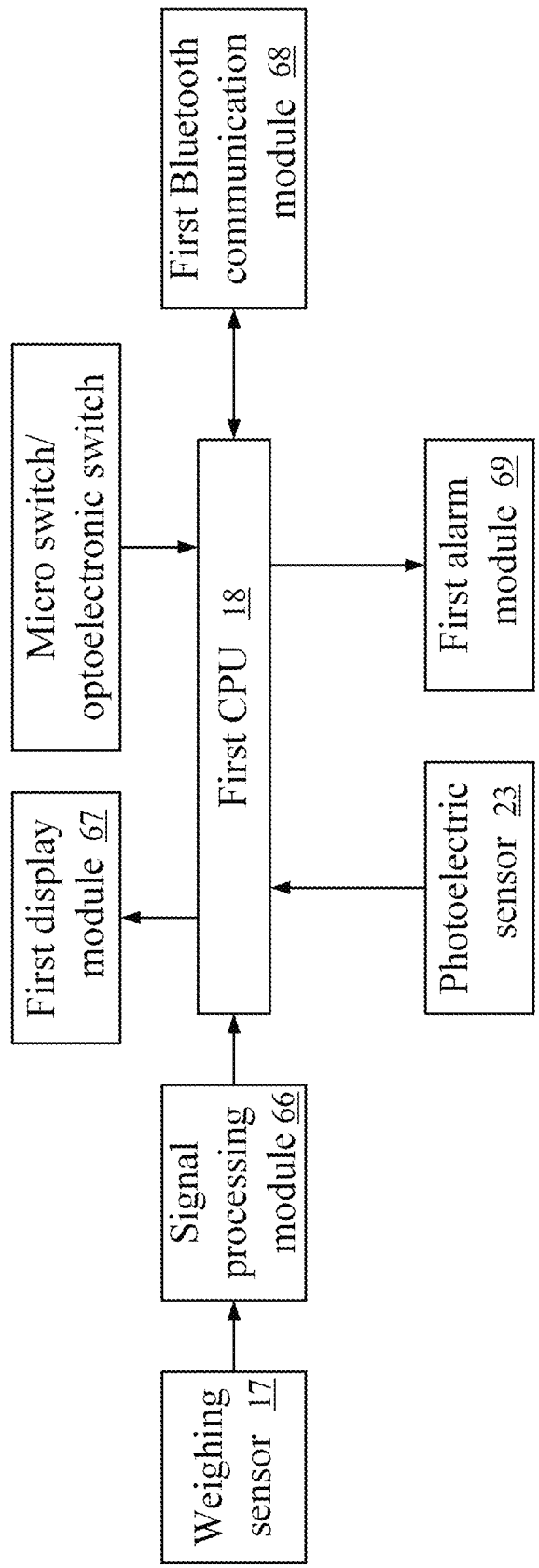
FIG. 14 is a schematic block diagram of a circuit of the flow measurement device according to the present disclosure.
Figure 15:
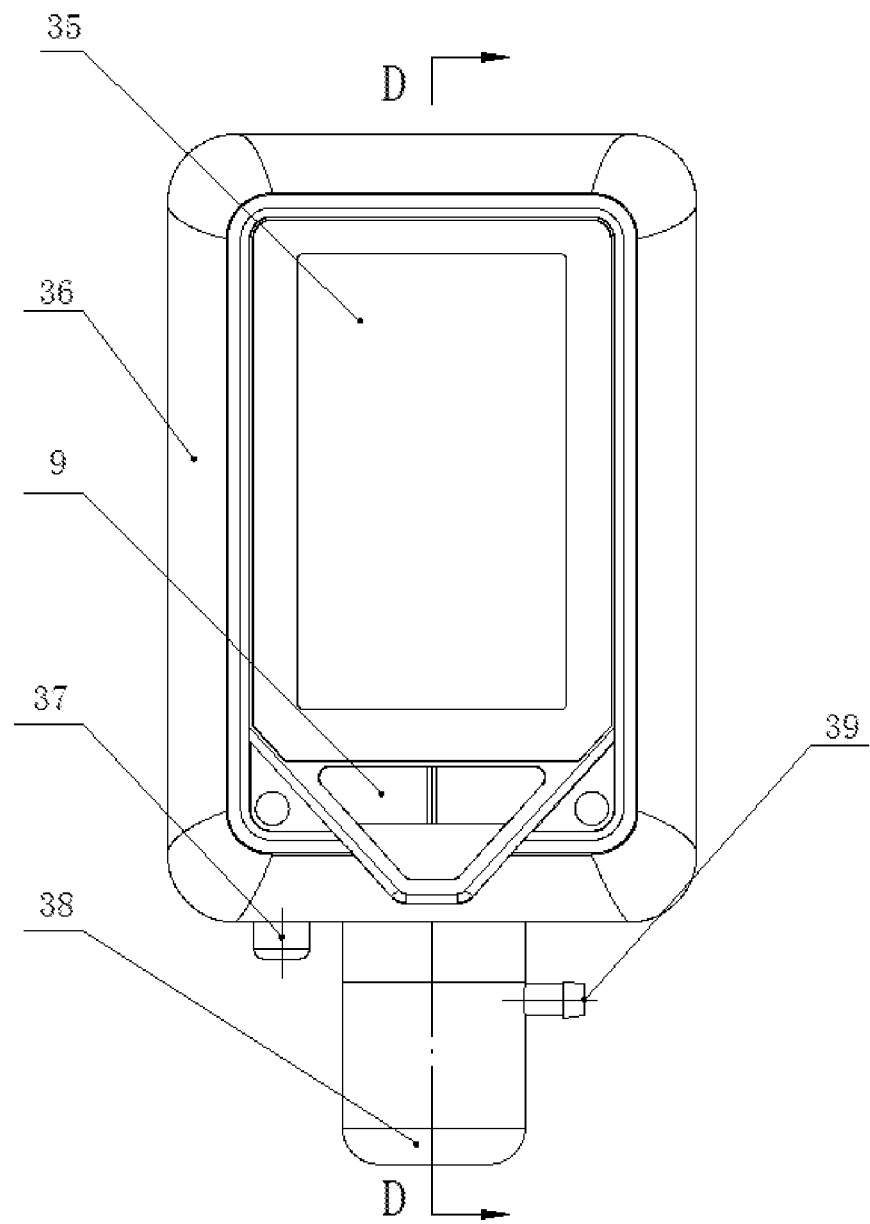
FIG. 15 is a structural schematic diagram of a controller according to the present disclosure.
Figure 16:
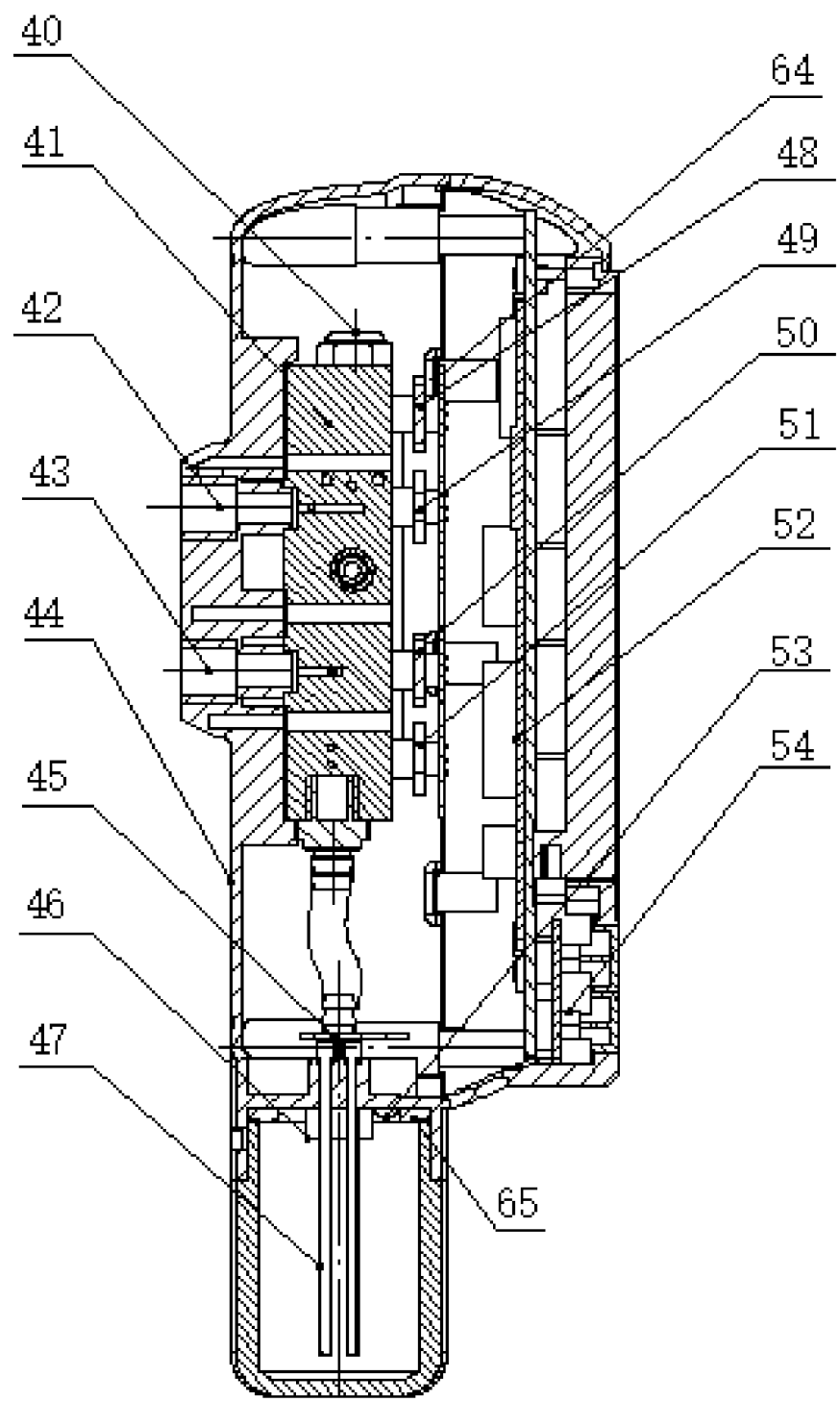
FIG. 16 is a cross-sectional view taken along a line D-D of FIG. 15.
Figure 17:
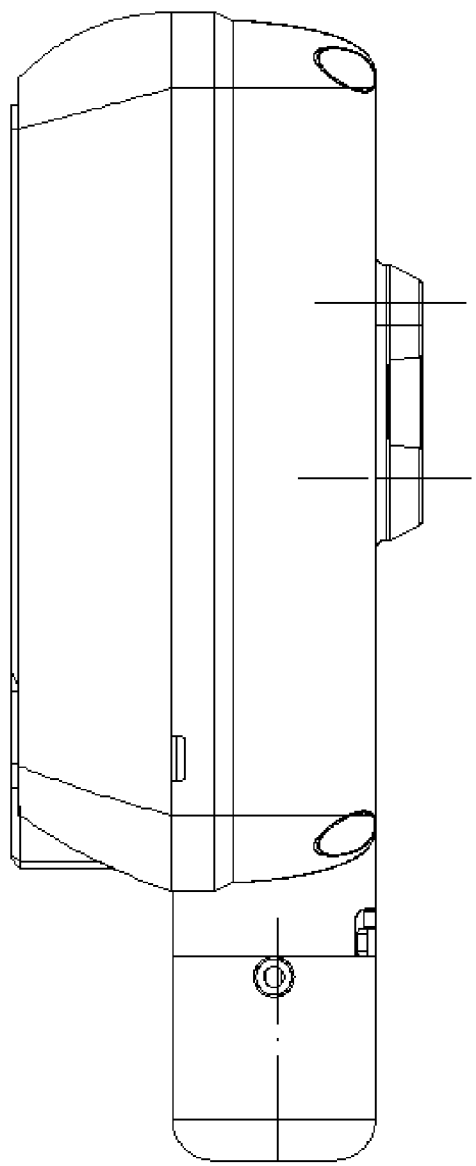
FIG. 17 is a right side view of FIG. 15.
Figure 18:
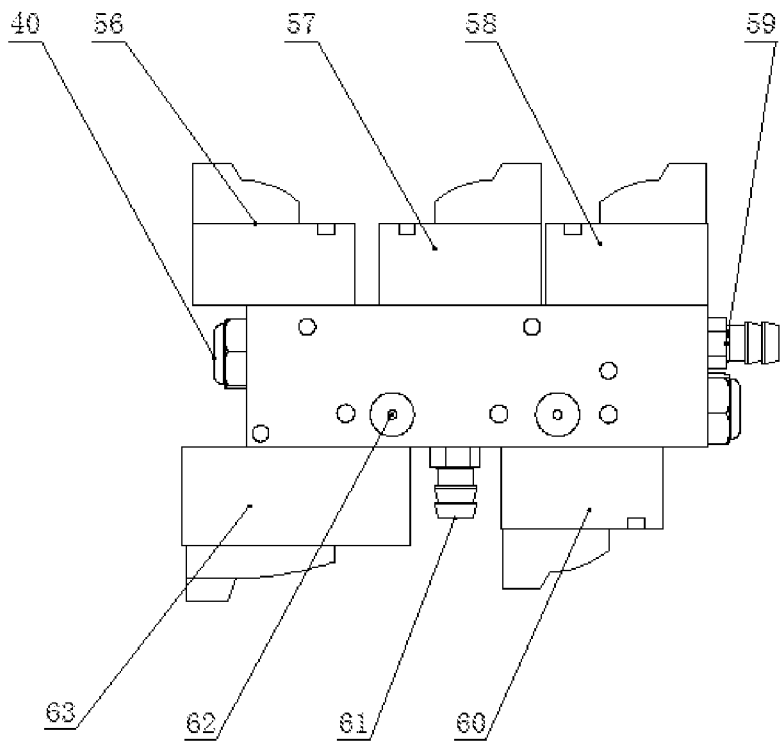
FIG. 18 is a structural schematic diagram of a pressure detection control module of the present disclosure.
Figure 19:
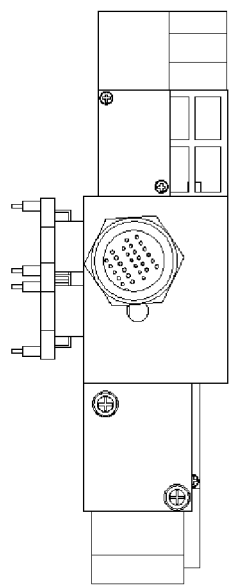
FIG. 19 is a left side view of FIG. 18.
Figure 20:
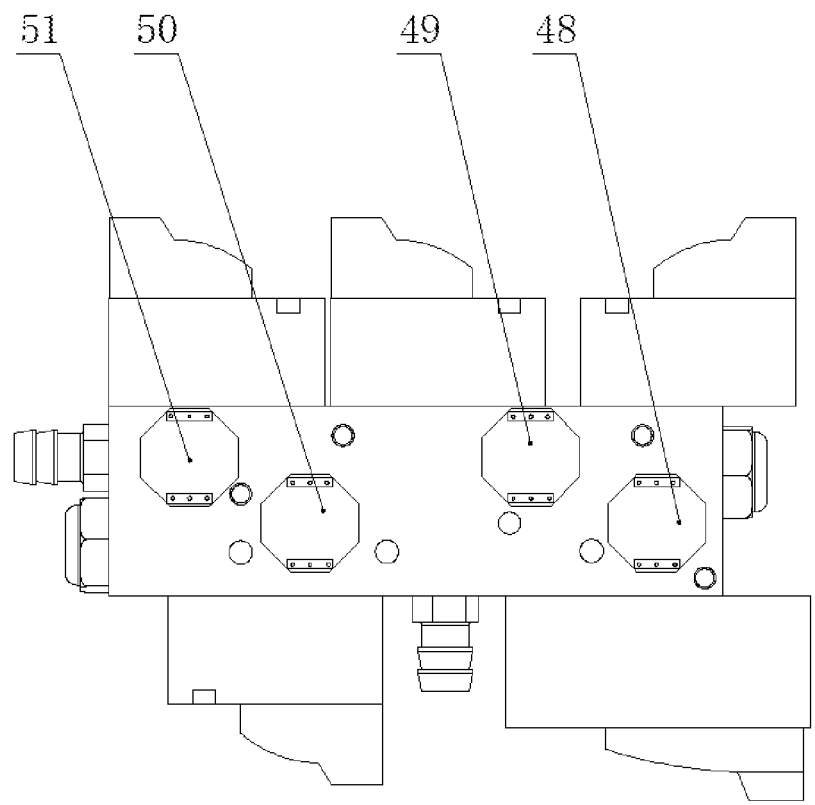
FIG. 20 is a rear view of FIG. 18.
Figure 21:
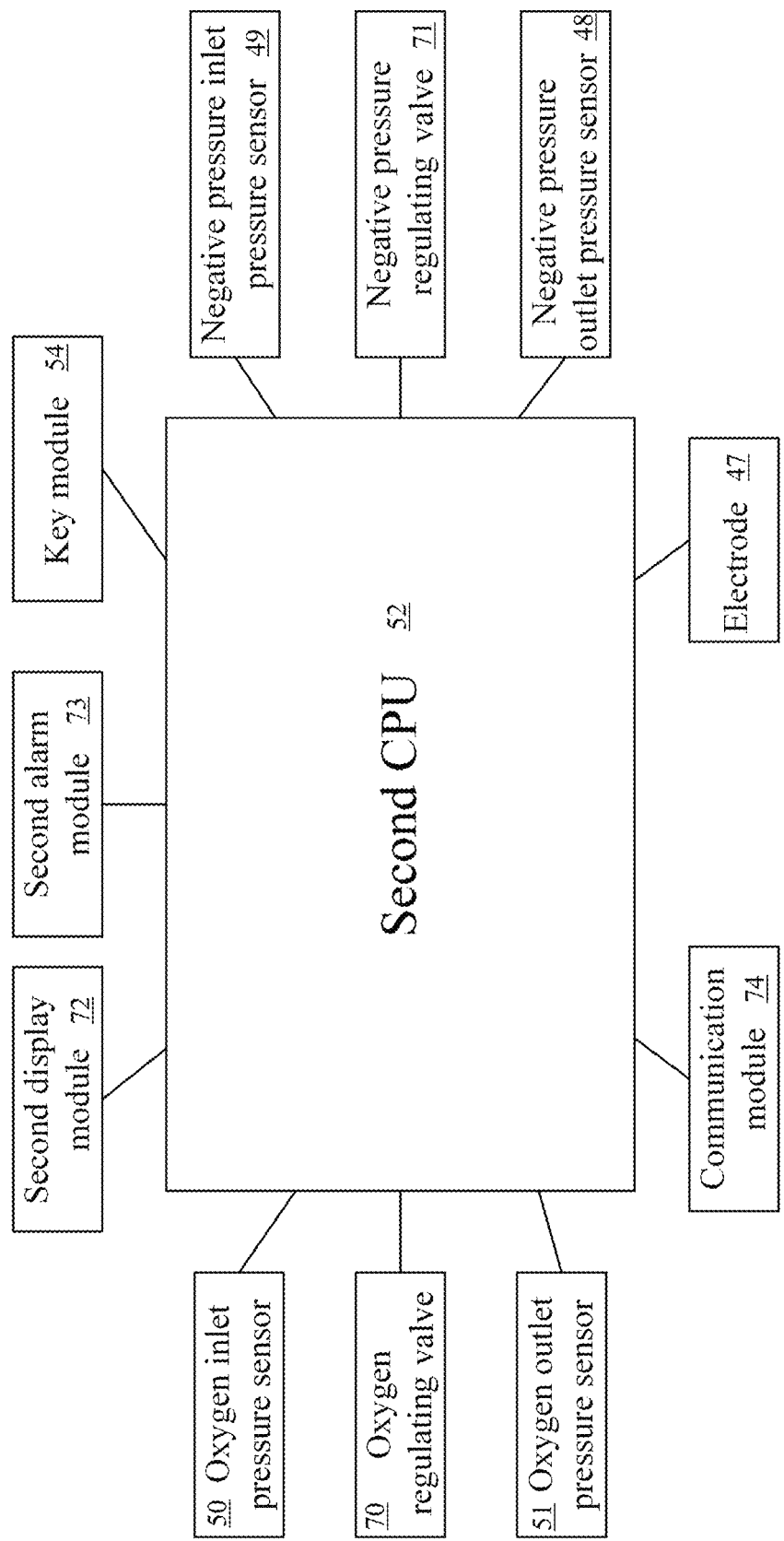
FIG. 21 is a schematic block diagram of a circuit of the controller according to the present disclosure.
Figure 22:
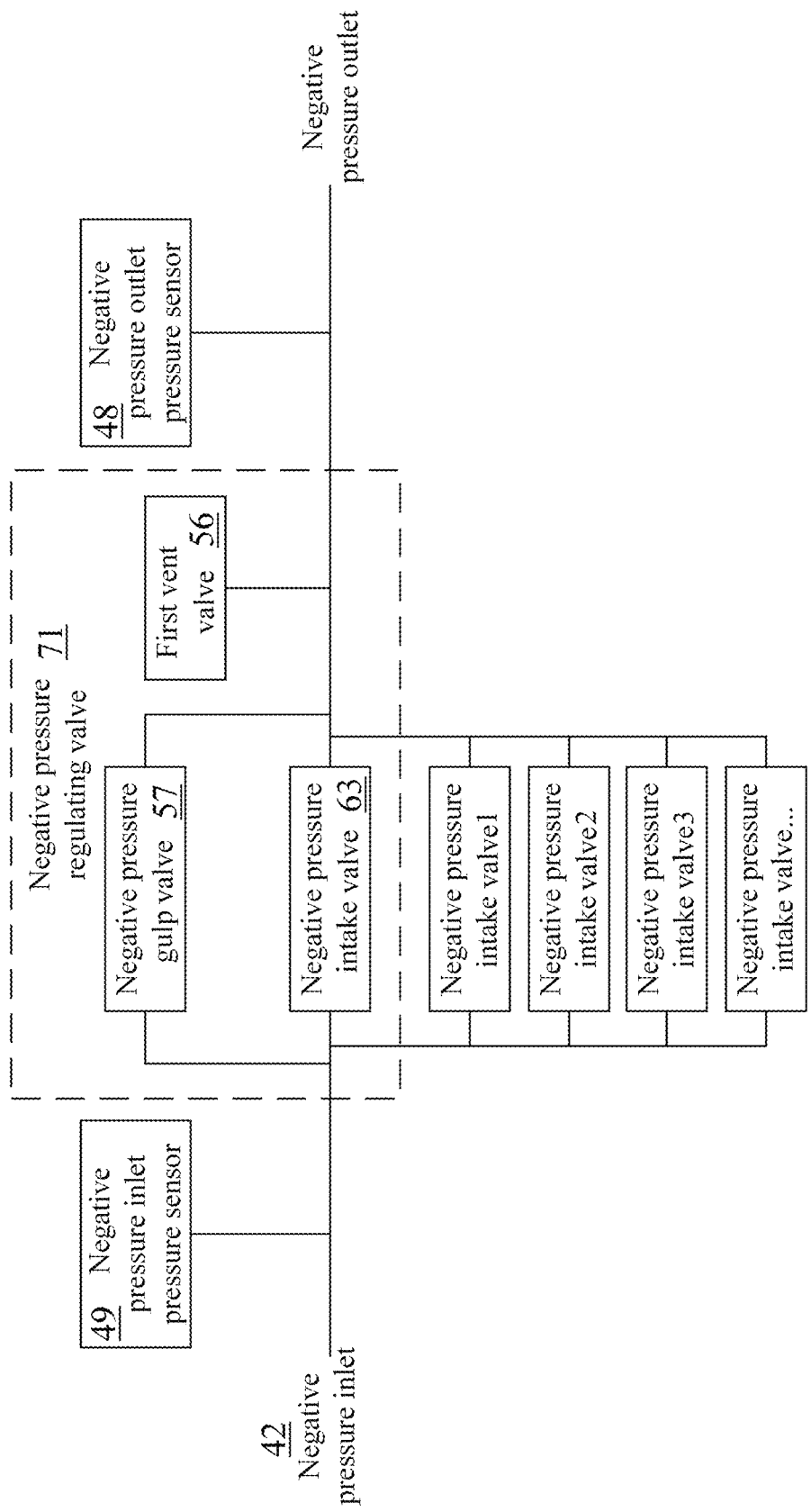
FIG. 22 is a schematic diagram of connections of each pressure sensor at a negative pressure regulating valve in the controller.
Figure 23:
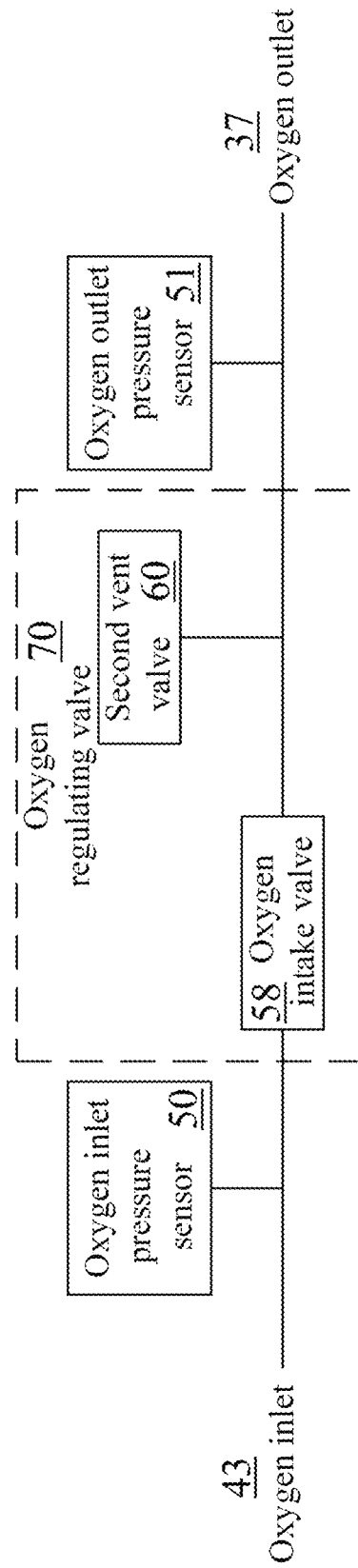
FIG. 23 is a schematic diagram of connections of each pressure sensor at an oxygen regulating valve in the controller.

List of reference numerals: 1 controller, 2 gas pipe, 3 flow measurement device, 4 bottle cap, 5 protection frame, 6 baffle plate, 7 bracket, 8 base, 9 key, 10 measurement liquid crystal display 11 liquid pipe fixing clamp, 12 liquid bottle, 13 negative pressure port, 14 liquid inlet, 15 splash-proof baffle, 16 mounting groove, 17 weighing sensor, 18 first CPU, 19 charging port, 20 conical floating head, 21 connecting rod, 22 float silicone head, 23 photoelectric sensor, 24 battery, 25 mounting slide groove, 26 clamp head, 27 protection frame body, 28 mounting block, 29 guard ring, 30 upper supporting plate, 31 lower supporting plate, 32 mounting through hole, 33 limiting protrusion, 34 guard plate, 35 controller liquid crystal display 36 front housing, 37 oxygen outlet, 38 overflow-proof bottle, 39 negative pressure air nozzle, 40 silencer, 41 electromagnetic valve group, 42 negative pressure inlet, 43 oxygen inlet, 44 rear housing, 45 electrode circuit board, 46 overflow-proof device, 47 electrode, 48 negative-pressure-outlet pressure sensor, 49 negative-pressure-inlet pressure sensor, 50 oxygen-inlet pressure sensor, 51 oxygen-outlet pressure sensor, 52 second CPU, 53 LED light, 54 key module, 55 float basket, 56 first vent valve, 57 negative pressure gulp valve, 58 oxygen intake valve, 59 oxygen outlet connector, 60 second vent valve, 61 negative-pressure-outlet connector, 62 negative-pressure-inlet connector, 63 negative pressure intake valve, 64 sealing gasket, 65 annular sealing ring, 66 signal processing module, 67 first display module, 68 first Bluetooth™ communication module, 69 first alarm module, 70 oxygen regulating valve, 71 negative pressure regulating valve, 72 second display module, 73, and 74.

DETAILED DESCRIPTION OF THE EMBODIMENTS

The embodiments of the present disclosure are further detailed below in combination with the drawings:

A multifunctional central suction system capable of remote monitoring is configured to include a flow measurement device 3 and a controller 1, a negative pressure port on the flow measurement device is connected to a negative pressure air nozzle 39 of the controller via a gas pipe 2. The flow measurement device includes a measurement mechanism and a liquid bottle 12. The negative pressure port is arranged on the liquid bottle, and the measurement mechanism is provided with a first BLUETOOTH® communication module. The controller is provided therein with a communication module 74 including a second BLUETOOTH® communication module and a Wi-Fi® communication module. The first BLUETOOTH® communication module of the measurement mechanism is in communication connection with the second BLUETOOTH® communication module of the controller. A model number of the second BLUETOOTH® communication module is DX-BT05, and a model number of the Wi-Fi® communication module is ESP8266MOD.

The measurement mechanism of the flow measurement device includes a base 8, a weighing monitoring unit, a bracket 7 and a battery 24. The weighing monitoring unit is powered by the battery arranged in the base. A weighing sensor of the weighing monitoring unit is provided on the base. The bracket is provided above the weighing sensor. Baffle plates 6 are evenly disposed at intervals circumferentially on an upper end surface of a bracket body of the bracket; and an area surrounded by the baffle plates forms a liquid bottle mounting area. The liquid bottle is mounted in the liquid bottle mounting area.

The base is a groove-type base, a guard plate 34 protruding upward is provided at a first side in a groove of the groove-type base, the weighing sensor 17 is provided at a second side opposite to the first side in the groove and is arranged perpendicularly to the guard plate in a plane. A height of the weighing sensor is higher than a height of the guard plate, a height difference between the weighting sensor and the guard plate is 1 mm.

The bracket includes an upper supporting plate 30 and a lower supporting plate 31 provided in one piece. A bottom of the lower supporting plate is provided with limiting protrusions 33 assembled at two ends of the weighing sensor. A mounting groove 16 is arranged in a middle of the upper supporting plate. Mounting through holes 32 leading to the lower supporting plate are arranged in the mounting groove and located between two limiting protrusions. The bracket is assembled with the weighing sensor in the base via a screw passing through the mounting through-hole. The baffle plates adapted to an outer diameter of a bottom of the liquid bottle are arranged circumferentially on the upper supporting plate.

The measurement mechanism further includes a protection frame 5. The protection frame includes a shell integrally formed with the base, a protection frame body 27 arranged on an inner wall of the shell, and a guard ring 29 arranged within the protection frame body via a mounting block 28.

The weighing monitoring unit includes the weighing sensor, a first CPU 18, a signal processor (i.e. signal processing module 66), a first display module 67, the first BLUETOOTH® communication module 68 and a first alarm module 69. An output terminal of the weighing sensor is connected to an input terminal of the signal processor. The output terminal of the signal processor is connected to the first CPU. The first BLUETOOTH® communication module is further provided on the first CPU. An output terminal of the first CPU is connected to the first display module and the first alarm module. The first display module includes a measurement liquid crystal display 10 and a key 9 mounted on the base.

The base is further provided with a charging port 19.

The liquid bottle includes a bottle body, a bottle cap 4, an overflow-proof protection mechanism and a full liquid protection mechanism. The overflow-proof protection mechanism includes an overflow-proof plug and a splash-proof baffle 15. The bottle cap is arranged on the bottle body, and provided with a liquid inlet 14 and a negative pressure port 13. The overflow-proof plug is arranged at the negative pressure port at a bottom of the bottle cap. The splash-proof baffle is arranged between the overflow-proof plug and the liquid inlet. The full liquid protection mechanism includes a photoelectric sensor 23 arranged on the protection frame and connected with the first CPU.

The overflow-proof plug includes a conical floating head 20, a connecting rod 21, a float silicone head 22 and a float basket 55. The float basket is mounted at a lower end of the negative pressure port. The connecting rod is mounted to the float basket via the float silicone head for limiting. The conical floating head integrally formed with the connecting rod is provided at a lower end of the connecting rod.

The system further includes a liquid pipe fixing clamp 11 made of rubber and plastic material. The liquid pipe fixing clamp includes a clamp head 26 formed with a clamping slot, and a mounting slide groove 25 arranged on a back of the clamp head and clamped on the protection frame.

The controller includes a housing, a pressure detection control module, a second CPU 52, a second display module 72 and a key module 54. A negative pressure inlet 42 and an oxygen inlet 43 is sequentially provided on a rear wall of the housing; an oxygen outlet 37 and a negative pressure outlet (at the negative pressure air nozzle 39) are sequentially provided at a bottom of the housing. The pressure detection control module is provided in the housing. Various corresponding electromagnetic valves of the pressure detection control module are connected to the corresponding negative pressure inlet, the corresponding oxygen inlet, the corresponding negative pressure outlet and the corresponding oxygen outlet via pipes, respectively. The pressure detection control module, the second display module and the key module are respectively connected to the second CPU arranged inside the housing. The second display module comprises a controller liquid crystal display 35 which is embedded into a front end surface of a front housing of the housing. The key module is arranged below the second display module on the front housing. The key module includes a key circuit board and a key. A model number of the second CPU is an STM32 series.

The pressure detection control module includes an electromagnetic valve group 41, a negative-pressure-inlet pressure sensor 49, a negative-pressure-outlet pressure sensor 48, an oxygen-inlet pressure sensor 50 and an oxygen-outlet pressure sensor 51. A silencer 40 is provided in the electromagnetic valve group 41 including a valve plate, a negative pressure regulating valve 71 and an oxygen regulating valve 70 provided on the valve plate. The negative pressure regulating valve includes a negative pressure intake valve 63, a negative pressure gulp valve 57, and a first vent valve 56. The negative pressure intake valve is connected in series with the first vent valve 56. The negative pressure gulp valve is connected in parallel to the negative pressure intake valve. The negative-pressure-inlet pressure sensor is provided on a pipe between the negative pressure inlet and a negative-pressure-inlet connector 62 at the negative pressure regulating valve. The negative-pressure-outlet pressure sensor is provided on a pipe between a negative-pressure-outlet connector 61 at the negative pressure regulating valve and the negative pressure outlet. The oxygen regulating valve includes an oxygen intake valve 58 and a second vent valve 60 connected in series. The oxygen-inlet pressure sensor is provided on a pipe between the oxygen inlet and the oxygen regulating valve. The oxygen-outlet pressure sensor is provided on a pipe between the oxygen outlet connector 59 at the oxygen regulating valve and the oxygen outlet. The negative pressure regulating valve, the oxygen regulating valve, the negative-pressure-inlet pressure sensor, the negative-pressure-outlet pressure sensor, the oxygen-inlet pressure sensor and the oxygen-outlet pressure sensor each are connected to the second CPU.

The negative pressure intake valve of the negative pressure regulating valve includes one negative pressure intake valve or more negative pressure intake valves connected in parallel. A first end of the negative pressure regulating valve is connected to the negative pressure inlet via a pipe, and a second end of the negative pressure regulating valve is connected to the negative pressure outlet via a pipe.

A sealing gasket 64 is provided at each valve port of the negative pressure regulating valve and the oxygen regulating valve.

The system further includes an electronic overflow-proof module. The electronic overflow-proof module includes an overflow-proof device 46, an electrode circuit board 45, electrodes 47 and an overflow-proof bottle 38. The overflow-proof device is provided at the negative pressure outlet. The electrodes are mounted on the overflow-proof device and connected to the electrode circuit board. The electrode circuit board is connected with the second CPU. The overflow-proof bottle 38 covering an exterior of the electrodes is arranged at the negative pressure outlet. A negative pressure air nozzle is mounted on a bottle body of the overflow-proof bottle via an annular sealing ring 65. The overflow-proof device 46 is an overflow-proof valve.

The system further includes a second alarm module 73 including an LED light 53 covered by the overflow-proof bottle and a buzzer in the housing, and the LED light and the buzzer are both connected to the second CPU.

The housing includes a front housing 36 and a rear housing 44 that are connected via screws.

In the present embodiments, the controller can acquire data from the flow measurement device via the first BLUETOOTH® communication module and the second BLUETOOTH® communication module provided, and transmit the data to a terminal such as Nurses Station via a Wi-Fi® module on the controller, facilitating a nurse to monitor and ensuring safety of a patient during drainage.

Although the embodiments and drawings of the present disclosure are disclosed for the purpose of illustration, it will be understood by those skilled in the art that various alternatives, changes and modifications are possible without departing from the spirit and scope of the present disclosure and the appended claims, and the scope of the present disclosure is thus not limited to the contents disclosed in the embodiments and the drawings.

What is claimed is:

1. A multifunctional central suction system capable of remote monitoring, comprising a flow measurement device and a controller, wherein a negative pressure port of the flow measurement device is connected to a negative pressure air nozzle of the controller via a gas pipe, the flow measurement device comprises a measurement mechanism and a liquid bottle, the negative pressure port is arranged on the liquid bottle; the measurement mechanism is provided with a first BLUETOOTH® communication module, a communication module comprising a second BLUETOOTH® communication module and a Wi-Fi® communication module is provided in the controller; the first BLUETOOTH® communication module on the measurement mechanism is in communication connection with the second BLUETOOTH® communication module in the controller;

wherein the controller comprises a housing, a pressure detection control module, a second CPU, a second display module and a key module for operating the controller; a negative pressure inlet and an oxygen inlet are provided sequentially on a wall of a rear housing of the housing; and an oxygen outlet and a negative pressure outlet are provided sequentially on a bottom of the housing; the pressure detection control module is provided in the housing, various corresponding electromagnetic valves of the pressure detection control module are connected to the negative pressure inlet, the oxygen inlet, the negative pressure outlet and the oxygen outlet via a pipe, respectively; the pressure detection control module, the second display module and the key module are respectively connected to the second CPU arranged inside the housing, the second display module is embedded into a front end surface of a front housing of the housing, the key module is arranged below the second display module on the front housing;

wherein the central suction system further comprises an electronic overflow-proof module, the electronic overflow-proof module comprises an overflow-proof device, an electrode circuit board, electrodes, and an overflow-proof bottle, the overflow-proof device is arranged at the negative pressure outlet, two electrodes are mounded on the overflow-proof device and connected with the electrode circuit board, the electrode circuit board is connected to the second CPU, and the overflow-proof bottle covering an exterior of the electrodes is arranged at the negative pressure outlet, a negative pressure air nozzle is provided on a bottle body of the overflow-proof bottle via a sealing device;

wherein the central suction system further comprises a second alarm module, the second alarm module comprises an LED light covered by the overflow-proof bottle and a buzzer in the housing, and the LED light and the buzzer are both connected to the second CPU;

wherein the measurement mechanism of the flow measurement device comprises a base, a weighing monitoring unit, a bracket and a battery, the weighing monitoring unit is powered by the battery arranged in the base, a weighing sensor of the weighing monitoring unit is provided on the base, the bracket is provided above the weighing sensor, and baffle plates are evenly and circumferentially disposed at an interval on an upper end surface of a bracket body of the bracket, an area surrounded by the baffle plates forms a mounting area for the liquid bottle, the liquid bottle is mounted in the mounting area; and wherein the base is a groove-type base, a guard plate protruding upward is provided at a first side in a groove of the groove-type base, the weighing sensor is provided at a second side opposite to the first side in the groove and is arranged perpendicularly to the guard plate in a plane, and a height of the weighing sensor is higher than a height of the guard plate.

2. The multifunctional central suction system according to claim 1, wherein the bracket comprises an upper supporting plate and a lower supporting plate provided in one piece, a bottom of the lower supporting plate is provided with limiting protrusions assembled at two ends of the weighing sensor, a mounting groove is arranged in a middle of the upper supporting plate, mounting through holes for leading to the lower supporting plate are arranged in the mounting groove and is located between two limiting protrusions, the bracket is assembled with the weighing sensor within the base via screw passing through the mounting through holes, the baffle plates adapted to an outer diameter of a bottom of the liquid bottle are arranged circumferentially on the upper supporting plate.

3. The multifunctional central suction system according to claim 1, wherein the measurement mechanism further comprises a protection frame; the protection frame comprises a shell integrally formed with the base, a protection frame body arranged on an inner wall of the shell, and a guard ring arranged on an inner periphery of the protection frame body via a mounting block.

4. The multifunctional central suction system according to claim 1, wherein the weighing monitoring unit comprises the weighing sensor, a first CPU, a signal processor, a first display module, and the first BLUETOOTH® communication module, an output terminal of the weighing sensor is connected to an input terminal of the signal processor, an output terminal of the signal processor is connected to the first CPU, the first BLUETOOTH® communication module is disposed on the first CPU, and the first display module comprises a measurement liquid crystal display and a key mounted on the base.

5. The multifunctional central suction system according to claim 1, wherein the base is further provided with a charging port thereon.

6. The multifunctional central suction system according to claim 1, wherein the liquid bottle comprises a bottle body, a bottle cap, an overflow-proof protection mechanism and a full liquid protection mechanism, the overflow-proof protection mechanism comprises an overflow-proof plug and a splash-proof baffle, the bottle cap is provided with a liquid inlet and the negative pressure port thereon, the overflow-proof plug is arranged at the negative pressure port at a bottom of the bottle cap, the splash-proof baffle is arranged between the overflow-proof plug and the liquid inlet; the full liquid protection mechanism comprises a photoelectric sensor arranged on the protection frame and connected with the first CPU.

7. The multifunctional central suction system according to claim 6, wherein the overflow-proof plug comprises a conical floating head, a connecting rod, a float silicone head and a float basket; the float basket is mounted at a lower end of the negative pressure port, the connecting rod is mounted to the float basket via the float silicone head for limiting and is provided with the conical floating head at a lower end of the connecting rod.

8. The multifunctional central suction system according to claim 3, further comprising a liquid pipe fixing clamp, the liquid pipe fixing clamp comprises a clamp head formed with a clamping slot and a mounting slide groove arranged on a back of the clamp head and clamped on the protection frame.

9. The multifunctional central suction system according to claim 1, wherein the key module comprises a key circuit board and a key; the pressure detection control module comprises a negative pressure detection control unit comprising a negative pressure regulating valve, a negative-pressure-inlet pressure sensor and a negative-pressure-outlet pressure sensor arranged on a valve plate; the negative pressure regulating valve comprises a negative pressure intake valve, a negative pressure gulp valve, and a first vent valve; the negative pressure intake valve is connected in series with the first vent valve and in parallel to the negative pressure gulp valve; the negative-pressure-inlet pressure sensor is arranged on a pipe between the negative pressure inlet and the negative pressure regulating valve; the negative-pressure-outlet pressure sensor is arranged on a pipe between the negative pressure regulating valve and the negative pressure outlet; the negative pressure regulating valve, the negative-pressure-inlet pressure sensor and the negative-pressure-outlet pressure sensor each are connected to the second CPU.

10. The multifunctional central suction system according to claim 9, wherein the pressure detection control module further comprises an oxygen detection control unit comprising an oxygen regulating valve, an oxygen-inlet pressure sensor and an oxygen-outlet pressure sensor arranged on the valve plate; the oxygen regulating valve comprises an oxygen intake valve and a second vent valve connected in series; the oxygen-inlet pressure sensor is arranged on a pipe between the oxygen inlet and the oxygen regulating valve; the oxygen-outlet pressure sensor is arranged on a pipe between the oxygen regulating valve and the oxygen outlet; the oxygen regulating valve, the oxygen-inlet pressure sensor and the oxygen-outlet pressure sensor each are connected to the second CPU.

11. The multifunctional central suction system according to claim 9, wherein the negative pressure intake valve of the negative pressure regulating valve comprises one negative pressure intake valve or more negative pressure intake valves connected in parallel.

12. The multifunctional central suction system according to claim 9, wherein a sealing device is provided at each valve port of the negative pressure regulating valve and the oxygen regulating valve.

13. The multifunctional central suction system according to claim 10, wherein a sealing device is provided at each valve port of the negative pressure regulating valve and the oxygen regulating valve.

* * * * *